United States Patent
Pedrotti et al.

(10) Patent No.: US 6,931,202 B2
(45) Date of Patent: Aug. 16, 2005

(54) ELECTRICAL EVAPORATOR WITH ADJUSTABLE EVAPORATION INTENSITY

(75) Inventors: Andrea Pedrotti, Pietramurata (IT); Stefano Baldessari, Caldonazzo (IT); Paolo Campedelli, Mori (IT); Stefano Ambrosi, Gardolo (IT); Filippo Stenico, Trento (IT)

(73) Assignee: S.C. Johnson & Son, Inc., Racine, WI (US)

( * ) Notice: Subject to any disclaimer, the term of this patent is extended or adjusted under 35 U.S.C. 154(b) by 257 days.

(21) Appl. No.: 10/267,445

(22) Filed: Oct. 9, 2002

(65) Prior Publication Data

US 2003/0138241 A1 Jul. 24, 2003

Related U.S. Application Data

(63) Continuation-in-part of application No. 09/916,275, filed on Jul. 30, 2001, now Pat. No. 6,466,739.
(60) Provisional application No. 60/371,162, filed on Apr. 10, 2002.

(30) Foreign Application Priority Data

Jul. 28, 2000 (IT) .................................... MI2000A1751

(51) Int. Cl.$^7$ ................................................. F24F 6/08
(52) U.S. Cl. ...................................... 392/395; 392/392
(58) Field of Search ................................. 392/386, 390, 392/392, 394, 395; 122/366; 239/34, 44, 49, 50

(56) References Cited

U.S. PATENT DOCUMENTS

| | | |
|---|---|---|
| 2,472,992 A | 6/1949 | Szekely ........................ 21/117 |
| 3,872,280 A | 3/1975 | Van Dalen ................... 219/271 |
| 4,968,487 A | 11/1990 | Yamamoto et al. .......... 422/125 |
| 5,038,394 A | 8/1991 | Hasegawa et al. .......... 392/395 |
| 5,095,647 A | 3/1992 | Zobele et al. .................. 43/125 |
| 5,114,625 A | 5/1992 | Gibson ........................ 261/30 |
| 5,222,186 A | 6/1993 | Schimanski et al. ........ 392/395 |
| 5,290,546 A | 3/1994 | Hasegawa et al. ......... 424/76.2 |
| 5,402,517 A | 3/1995 | Gillett et al. ................ 392/386 |
| 5,647,053 A | 7/1997 | Schroeder et al. .......... 392/390 |
| 5,909,845 A * | 6/1999 | Greatbatch et al. ........... 239/44 |
| 6,104,867 A | 8/2000 | Stathakis et al. ............ 392/403 |
| 6,145,241 A | 11/2000 | Okuno ........................ 43/129 |
| 6,278,840 B1 | 8/2001 | Basagañas Millan ....... 392/390 |
| 6,285,830 B1 | 9/2001 | Basagañas Millan ....... 392/395 |
| 6,361,752 B1 * | 3/2002 | Demarest et al. ........... 422/306 |
| 6,446,583 B2 | 9/2002 | Vieira ........................ 122/366 |
| 6,466,739 B2 * | 10/2002 | Ambrosi et al. ............ 392/395 |
| 6,567,613 B2 | 5/2003 | Rymer ........................ 392/390 |
| 6,580,875 B2 | 6/2003 | Rymer ........................ 392/395 |

FOREIGN PATENT DOCUMENTS

| | | |
|---|---|---|
| EP | 0 943 344 A1 | 9/1999 |
| EP | 0 962 132 A1 | 12/1999 |
| EP | 1 175 833 A1 | 1/2002 |
| ES | 1 005 422 | 11/1988 |
| WO | WO 98/19526 | 5/1998 |
| WO | WO 03/061716 | 7/2003 |

* cited by examiner

*Primary Examiner*—Sang Y. Paik

(57) ABSTRACT

An evaporator includes a housing, a bottle containing a substance to be evaporated, a wick having a lower portion disposed within the bottle and an upper portion protruding from the bottle, a heating device disposed within the housing at a position proximate to the upper portion of the wick, and an adjustment mechanism within the housing for displacing at least the upper portion of the wick toward or away from the heating device in a direction substantially perpendicular to the longitudinal axis of the wick. In a preferred embodiment, the adjustment mechanism includes a hollow cylindrical portion that engages the upper portion of the wick, and a dial portion for rotating the hollow cylindrical portion about an axis of rotation.

53 Claims, 13 Drawing Sheets

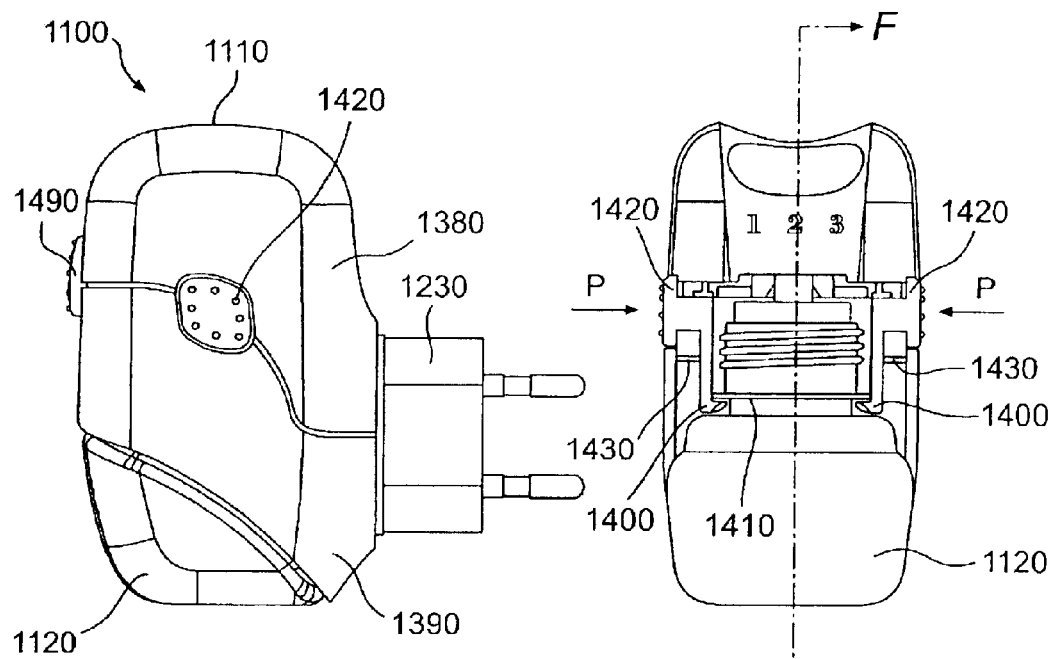
FIG. 12
FIG. 13
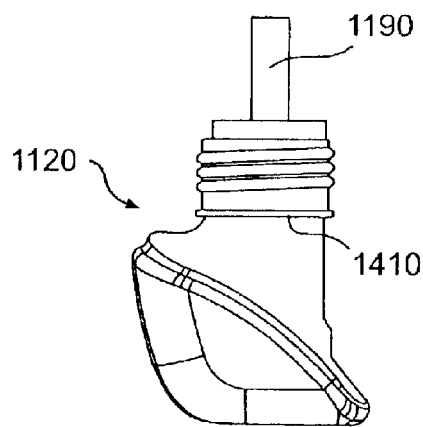
FIG. 14

ELECTRICAL EVAPORATOR WITH ADJUSTABLE EVAPORATION INTENSITY

This application is a continuation-in-part of U.S. patent application Ser. No. 09/916,275, filed Jul. 30, 2001 now U.S. Pat. No. 6,466,739. This application also claims the benefit of U.S. Provisional Patent Application No. 60/371,162, filed Apr. 10, 2002.

BACKGROUND OF THE INVENTION

1. Field of the Invention

The present invention relates generally to an electrical evaporator for use with liquid formulations containing a chemical active such as an insecticide, a fragrance, an odor eliminator, or the like, and, in particular, to an electrical evaporator having an adjustable intensity feature that enables variation of the evaporation rate of the liquid formulation between a minimum and maximum level.

2. Description of the Related Art

Electrical evaporators in which the evaporation rate of a liquid formulation from a wick can be adjusted by varying the relative positions of a heating device and the wick are known.

For example, Spanish Utility Model No. 1 005 422 discloses an evaporator in which a heating device and a wick can be moved vertically relative to one another by means of a mechanical device, such as a screw/nut thread mechanism, in order to increase or decrease the heat intensity to which the wick is exposed. European Patent Publication No. 0 942 648, by contrast, discloses an evaporator in which a heating device remains stationary while a wick and bottle are displaced vertically in the direction of the longitudinal axis of the wick using a screw/nut thread mechanism, thereby increasing or reducing the overlap between the wick and the heating device. Still another type of evaporator is disclosed in European Patent Publication No. 0 943 344. In that evaporator, a heating device is mounted on a plug which can be moved toward or away from a wick. A drawback of all of these known devices, however, is that they are relatively expensive to manufacture, due in part to the complex screw/nut thread mechanisms of the first two evaporator types and the specially-designed plug of the third evaporator type.

SUMMARY OF THE INVENTION

The present invention provides an electrical evaporator having an improved adjustment mechanism for varying the evaporation rate of the liquid formulation.

According to one aspect of the invention, an evaporator, for use with a bottle containing a substance to be evaporated and a wick that has its lower portion disposed within the bottle and its upper portion protruding from the bottle, includes (i) a housing, (ii) a heating device disposed within the housing at a position proximate to the upper portion of the wick, and (iii) an adjustment mechanism within the housing for displacing at least the upper portion of the wick toward or away from the heating device in a direction substantially perpendicular to the longitudinal axis of the wick.

In another aspect, the present invention relates to an evaporator including (i) a housing, (ii) a bottle containing a substance to be evaporated, (iii) a wick, having a lower portion disposed within the bottle and an upper portion protruding from the bottle, for drawing the substance to be evaporated toward the upper portion of the wick, (iv) means for heating the upper portion of the wick to evaporate the substance, (v) means for positioning the upper portion of the wick relative to the heating means, and (vi) means for displacing at least the upper portion of the wick toward or away from the heating means in a direction substantially perpendicular to the longitudinal axis of the wick.

In still another aspect, the present invention relates to a plug-in evaporator for vaporizing a liquid formulation. The evaporator includes (i) a bottle containing a liquid formulation, (ii) a wick, having a lower portion disposed within the bottle and an upper portion protruding from the bottle, for drawing the liquid formulation from the bottle toward the upper portion of the wick, and (iii) a housing in which the bottle is retained. The housing includes (a) an electrical heating device positioned proximate to the upper portion of the wick, (b) an electrical plug for supplying power to the heating device and for supporting the evaporator in an electrical outlet, and (c) an adjustment mechanism for displacing the upper portion of the wick toward or away from the heating device in a direction substantially perpendicular to the longitudinal axis of the wick.

In a further aspect, the present invention relates to a plug-in evaporator for dispersing a chemical active into a surrounding environment. The evaporator includes (i) a bottle containing a liquid formulation, (ii) a wick, having a lower portion disposed within the bottle and an upper portion protruding from the bottle, for drawing the liquid formulation from the bottle toward the upper portion of the wick, (iii) a housing in which the bottle is detachably retained, (iv) an electrical heating device disposed within the housing at a position proximate to the upper portion of the wick, (v) an electrical plug extending from the housing for supplying power to the heating device and for supporting the evaporator in an electrical outlet, and (vi) an adjustment mechanism within the housing for displacing the upper portion of the wick toward or away from the heating device in a direction substantially perpendicular to the longitudinal axis of the wick. The adjustment mechanism includes (a) a hollow cylindrical portion that engages the upper portion of the wick, and (b) a dial portion for rotating the hollow cylindrical portion about an axis of rotation. The hollow cylindrical portion defines an opening through which the wick extends, and, preferably, the center of that opening is offset relative to the axis of rotation of the hollow cylindrical portion.

A better understanding of these and other features and advantages of the invention may be had by reference to the drawings and to the accompanying description, in which preferred embodiments of the invention are illustrated and described.

BRIEF DESCRIPTION OF THE DRAWINGS

FIG. 12 is a side elevation view of an evaporator according to a second preferred embodiment of the present invention.

FIG. 13 is a rear view of the evaporator shown in FIG. 12, with part of the bottom shell of the evaporator and the actuating pushbutton removed, in order to show more clearly how the bottle is held within the evaporator.

FIG. 14 is a side elevation view of the bottle used in the evaporator shown in FIG. 12.

Throughout the figures, like or corresponding reference numerals have been used for like or corresponding parts.

DESCRIPTION OF THE PREFERRED EMBODIMENTS

An evaporator 100 according to a first preferred embodiment of the present invention is illustrated in FIGS. 1–11.

Figure 1:
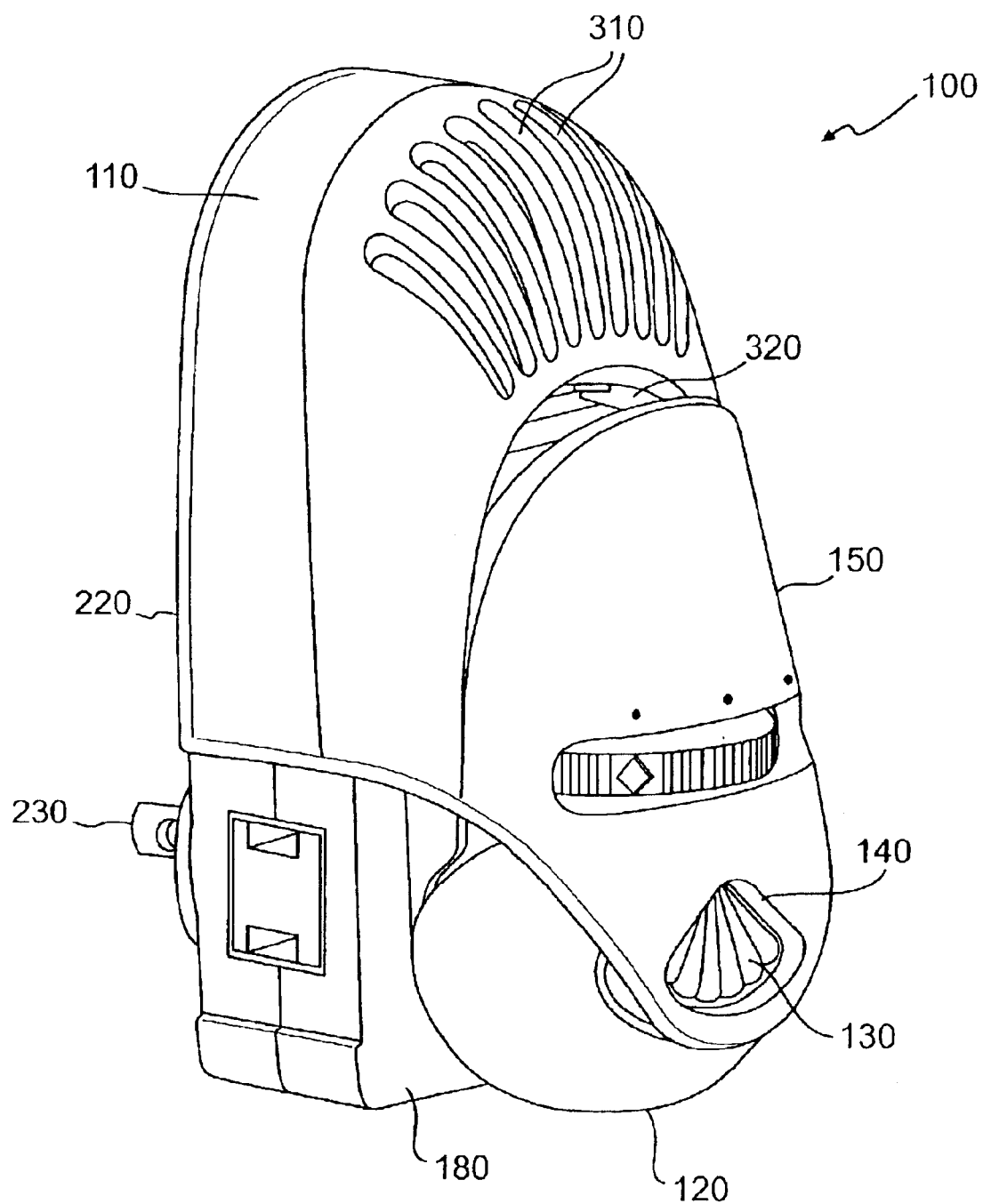
FIG. 1 is a perspective view of an evaporator according to a first preferred embodiment of the present invention.

As shown in FIG. 1, the evaporator 100 comprises a multi-piece housing 110 in which a bottle 120 is detachably retained. The bottle 120 contains an evaporable substance (not shown), such as, for example, a liquid formulation including a chemical active such as an insecticide, fragrance, odor eliminator, or the like. The term "bottle" is used herein in its broadest possible sense, including any receptacle, container, pouch, etc., capable of holding a liquid formulation. A raised pattern 130 on one side of the bottle is engaged by an opening 140 in a front shell 150 of the evaporator housing 110, while a similar raised pattern 160 (shown in FIG. 6) on an opposite side of the bottle 120 is engaged by a recess 170 (shown in FIG. 3) in a middle shell 180, in order to secure the bottle 120 within the evaporator 100. The front shell 150 is sufficiently pliant so that pulling the bottle 120 in a downward direction causes the raised patterns 130, 160 to release from the opening 140 in the front shell 150 and the recess 170 in the middle shell 180, respectively, thereby enabling removal of the bottle 120 from the evaporator 100. Alternatively, the neck portion of the bottle may be designed to snap or screw into the evaporator housing. Suitable refill bottles are available in a wide variety of liquid formulations from S.C. Johnson & Son, Inc., of Racine, Wis., under the GLADE® PLUGINS® and RAID® brand names.

Figure 3:
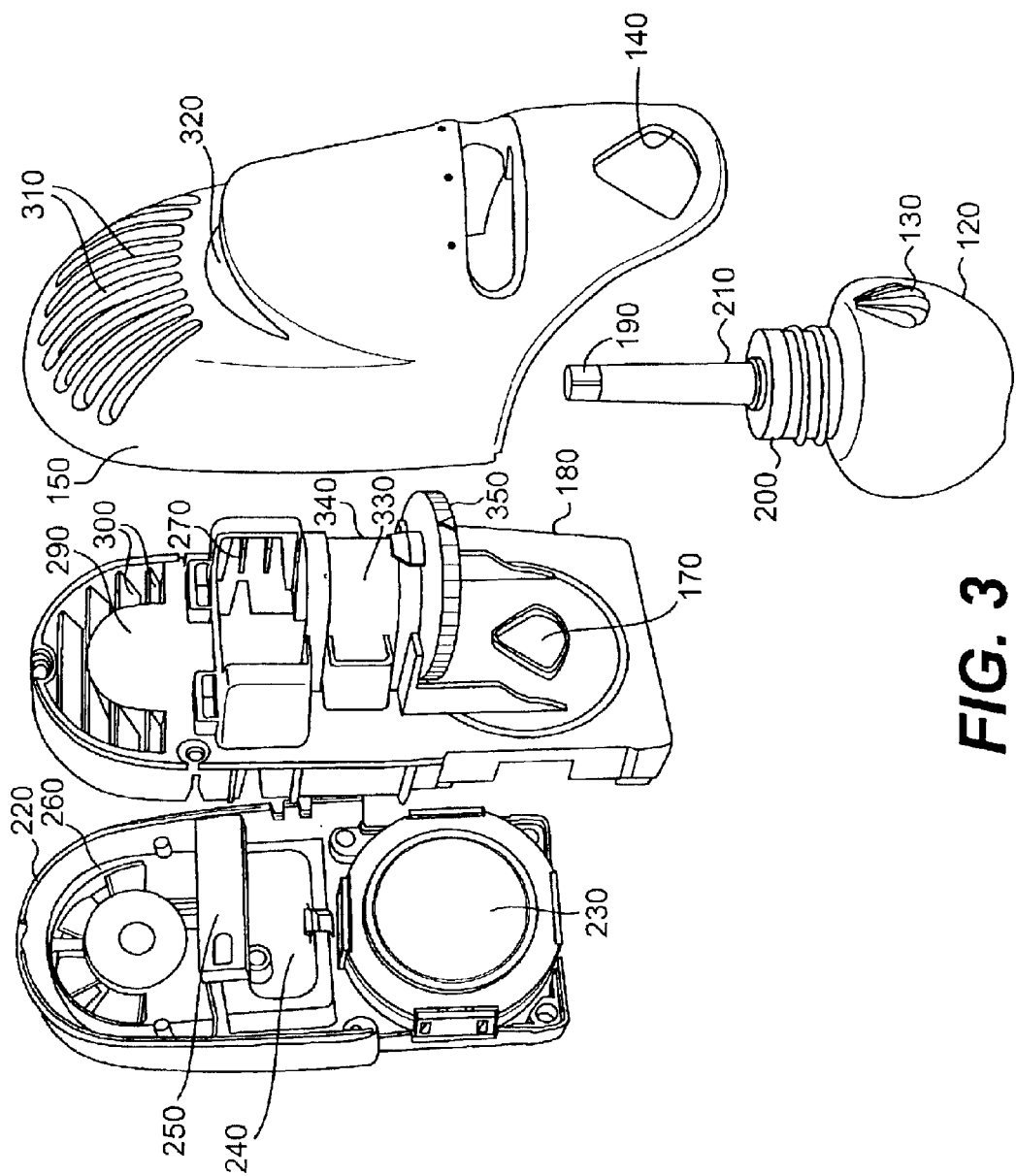
FIG. 3 is an exploded assembly view of the evaporator shown in FIG. 1.
Figure 4:
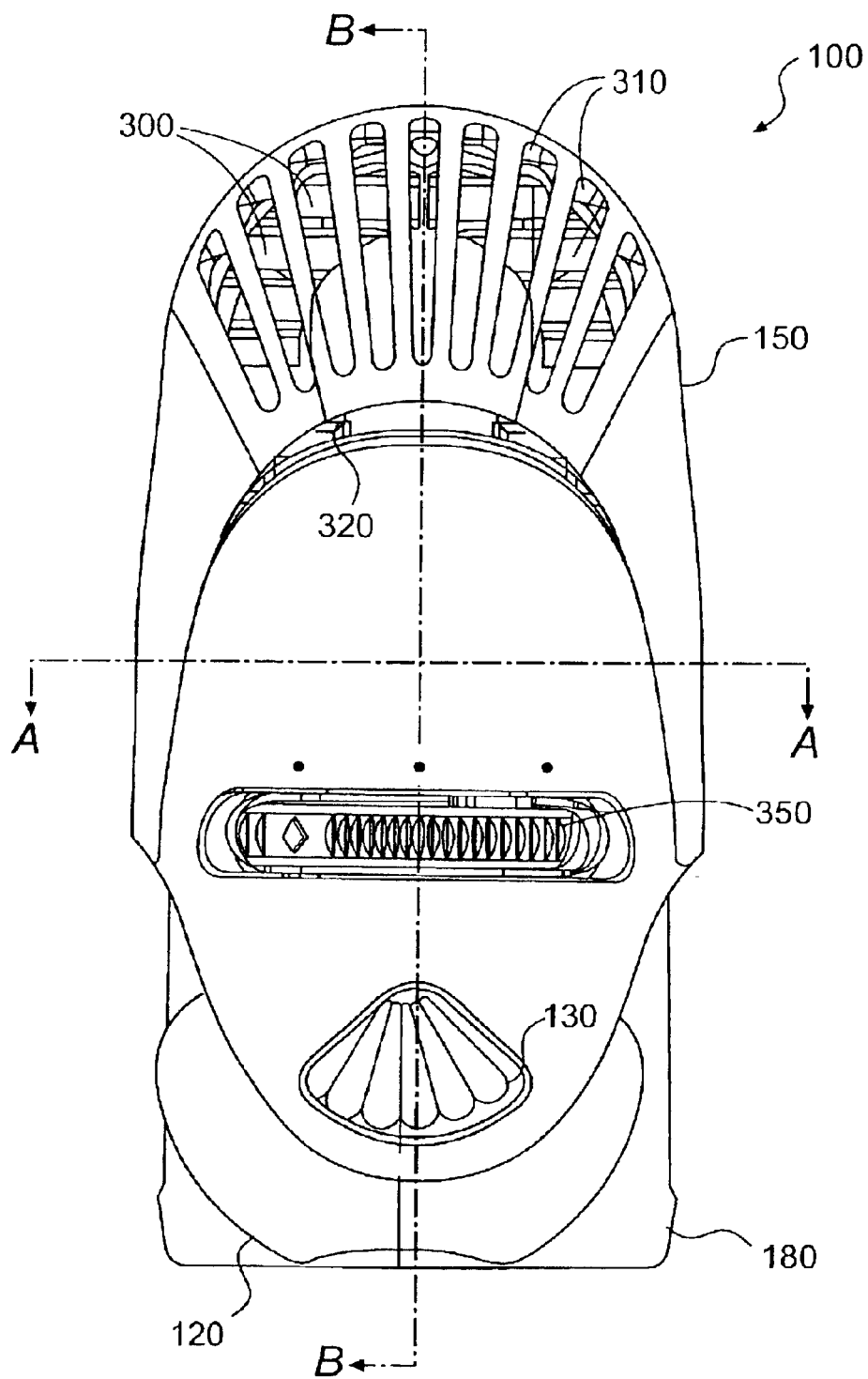
FIG. 4 is a front elevation view of the evaporator shown in FIG. 1, with the intensity setting on low.

As shown in FIG. 3, the bottle 120 includes a wick 190 for drawing the liquid formulation out of the bottle 120 and toward an upper portion of the wick 190. A lower portion of the wick 190 is immersed in the liquid formulation, and the upper portion of the wick 190 protrudes above the neck of the bottle 120. Preferably, the wick 190 is positioned within the bottle 120 by a cap 200 which includes a sheath 210 that encases the upper portion of the wick 190, except for an open area near the tip of the wick 190. Alternatively, a cap without a sheath can be utilized. Preferably, the wick is about 7 mm in diameter and is constructed of ultra high molecular weight high density polyethylene.

In the preferred embodiment illustrated in FIGS. 1–10, the evaporator housing 110 comprises three shells—the front and middle shells 150, 180 noted above and a back shell 220—which are fastened together by heat-staking or any other suitable fastening means, including, for example, rivets, press fit, snap fit, screws, ultrasonic welding, adhesives, or the like. The electrical components (discussed in more detail below) of the evaporator 100 are housed within the space enclosed by the middle and back shells 180, 220.

Figure 2:
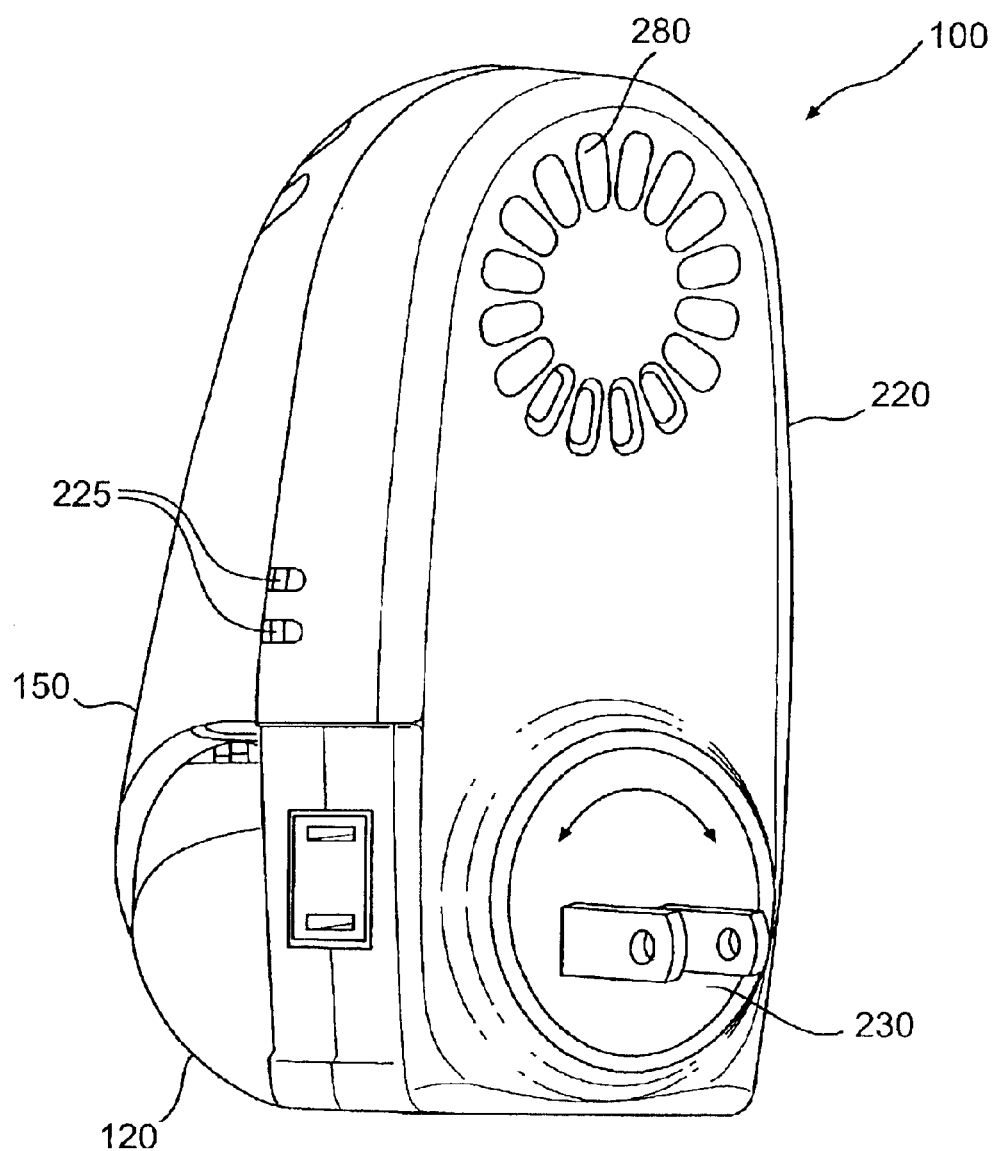
FIG. 2 is a rotated perspective view of the evaporator shown in FIG. 1.

Referring to FIG. 2, the back shell 220 contains a circular opening in which a known electrical plug assembly 230 is seated. The plug 230 serves the dual purpose of supplying power to the electrical components of the evaporator 100 and also supporting the evaporator 100 in a wall outlet (not shown). Preferably, the plug assembly 230 is rotatable 360 degrees in order to support the evaporator 100 in an upright position in both horizontal and vertical wall outlets. Advantageously, the plug assembly 230 can be provided with an extra outlet which, as illustrated in FIG. 1, is located on the side of the evaporator 100 when the evaporator is plugged into a vertical wall outlet, and on the bottom of the evaporator 100 when the evaporator is plugged into a horizontal wall outlet (not shown).

As schematically illustrated in FIG. 3, the plug assembly 230 is electrically connected to a circuit board 240, which, in turn, is electrically connected to a heating device 250 and, preferably, also to a fan unit 260. The heating device 250 is disposed adjacent to a window 270 in the middle shell 180 which faces the tip of the wick 190 when the bottle 120 is inserted in the evaporator 100. Heating the wick 190 enhances the rate at which the liquid formulation evaporates into the surrounding environment, as described more fully below. Preferably, the heating device 250 is a 1.9 k, 7 W metal oxide resistor potted in a ceramic block. The resistor preferably has PTC (positive temperature coefficient) characteristics, meaning that its resistance value increases slightly as the resistor heats up. A suitable resistor is available from Great Land Enterprise Co., Ltd., of Shenzhen, China, for example. Alternatively, the heating device 250 can comprise one or more other types of resistor heaters, a wire-wound heater, a PTC heater, or the like.

The fan unit 260 is disposed within an upper portion of the housing 110. The back shell 220 includes air inlets 280 (shown in FIG. 2) for supplying air to the fan unit 260. As described more fully below, the fan unit 260 creates an airstream that entrains the evaporated liquid formulation and assists in the dispersion of the chemical active into the surrounding environment. Preferably, the flow rate of the fan unit 260 within the evaporator 100 is approximately 0.5 cubic feet per minute, and the fan speed is approximately 2800–3800 RPM. A suitable fan unit 260 is a 12 V, DC, brushless fan, such as available from Power Logic Tech. Inc., of Tapei-Hsien, Taiwan. Alternatively, other DC or AC fans could be utilized, with appropriate adjustments to the circuit board 240, which is described more fully below.

Figure 11:
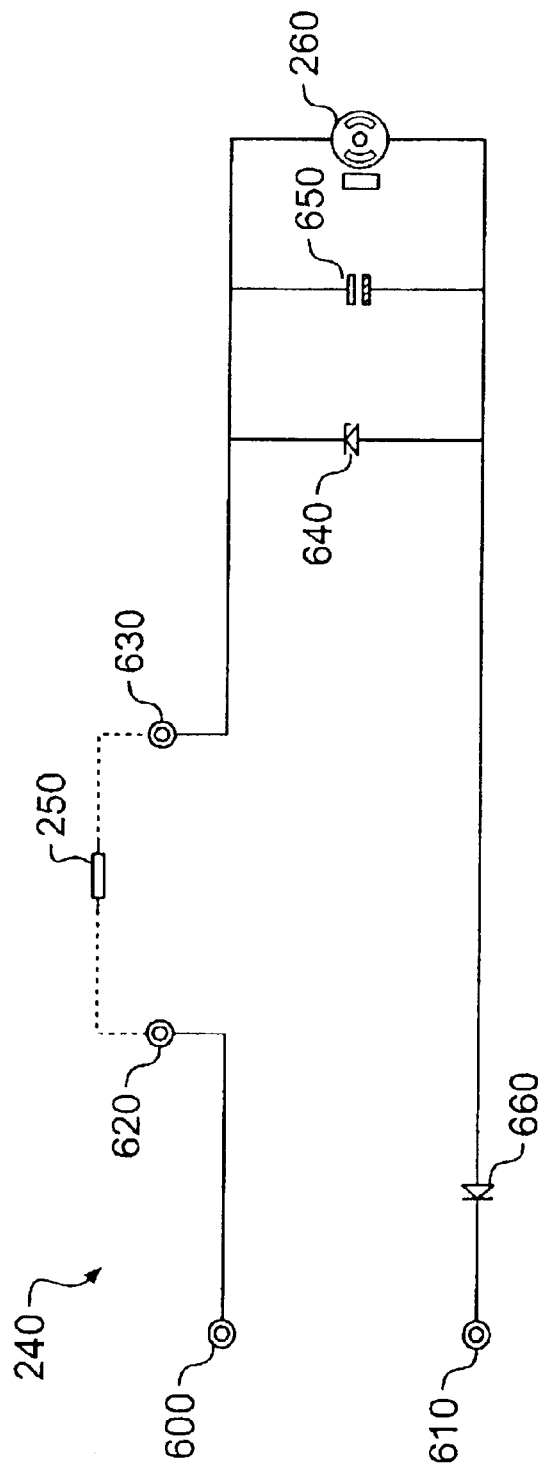
FIG. 11 is a schematic diagram of a preferred electrical circuit for the evaporator shown in FIG. 1.

FIG. 11 is a schematic diagram of a preferred circuit board 240 for the evaporator 100. Preferably, the circuit board 240 is constructed of a flame-rated material. The circuit board 240 includes pins 600, 610 that connect to bus bars (not shown) of the plug assembly 230. The voltage applied across the pins 600, 610 is 120 V, at a frequency of 60 Hz. The heating device 250 is connected to the circuit board 240 by a pair of rivets 620, 630. Connected in parallel are (i) a 15 V, 1.3 W Zener diode 640, (ii) a 22 μF, 50 V aluminum electrolytic capacitor 650, rated for a temperature of 105 C, and (iii) the fan unit 260. The circuit board 240 also includes a 1N 4007 diode 660. The power consumption across the entire circuit is about 3.5 W to about 4.0 W. Those skilled in the art will appreciate that numerous alternative circuit configurations are also possible.

Figure 10:
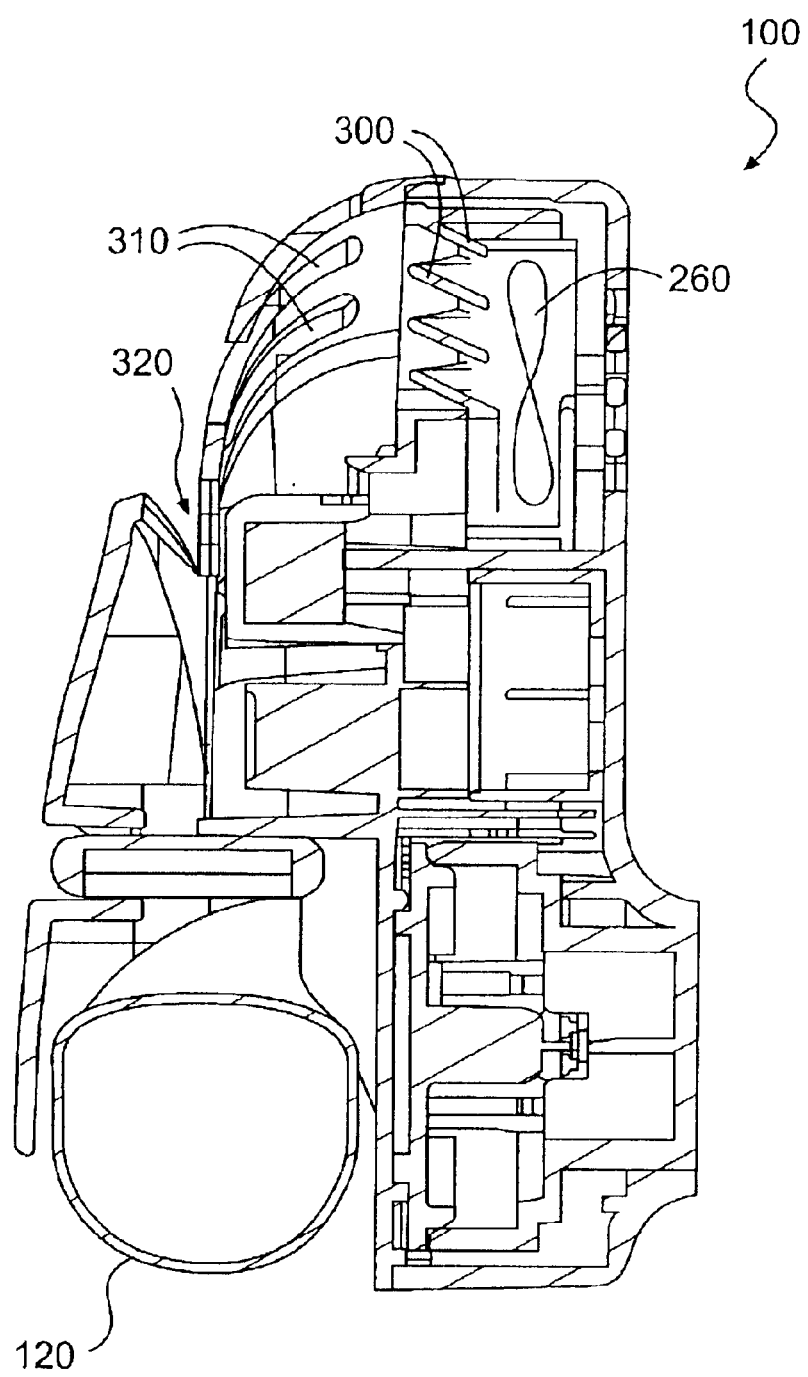
FIG. 10 is a cross-sectional view taken along section line E—E in FIG. 7.

Immediately downstream of the fan unit 260 is a louver structure 290, shown in FIG. 3, comprising at least one louver and, more preferably, a plurality of louvers 300. Preferably, the louver structure 290 is an integral part of the middle shell 150, but it can also be provided separately from the middle shell 150. As illustrated in FIGS. 3 and 10, the louvers 300 are angled upwardly and away from the heating device 250 and the upper portion of the wick 190, preferably at an angle between about 20 degrees to about 60 degrees relative to horizontal when the evaporator 100 is in an upright position.

The optimum louver angle varies depending on such factors as the fan speed and the air exchange rate within the room in which the evaporator 100 is located. In rooms with relatively low air exchange rates (e.g., between about 0.6 to about 1.2 exchanges per hour), a louver angle of about 40 degrees to about 45 degrees relative to horizontal is preferred. In rooms with higher air exchange rates, a louver angle of about 25 degrees to about 30 degrees relative to horizontal is preferred.

The middle shell 180 is shaped so as to direct the airstream created by the fan unit 260 through the louvers 300. Notably, the middle shell 180 does not permit stray currents of air to recirculate within the housing 110, where those currents could have an undesirable cooling effect on the heating device 250. A pair of openings 225 (shown in FIG. 2) in the side of the evaporator 100 helps to achieve proper air circulation through the evaporator.

The front shell 150 includes a plurality of vents 310 through which the airstream exits the evaporator 100 after passing through the louvers 300. As the airstream exits the evaporator 100 through the vents 310, it entrains the evaporated liquid formulation, which rises from the wick 190 through an opening 320 in the front shell 150 below the vents 310.

Tests have demonstrated that an evaporator constructed in accordance with the present invention disperses higher concentrations of the chemical active within the central "living area" of a room, as opposed to the walls, floor, or ceiling.

Those skilled in the art will appreciate that the benefits of the fan unit 260 and louver structure 290 described above can be achieved even in the absence of a heating device 250.

Optionally, the evaporator 100 also includes an adjustment mechanism 330 that positions the upper portion of the wick 190 with respect to the heating device 250. Preferably, the adjustment mechanism 330 includes a hollow cylindrical portion 340 that surrounds and engages part of the upper portion of the wick 190, preferably at a location where the wick 190 is encased by the sheath 210. The adjustment mechanism 330 also includes a dial portion 350, accessible from outside the evaporator housing 110, for rotating the cylindrical portion 340 about an axis of rotation. The dial portion 350 preferably is formed integrally with the cylindrical portion 340, although it need not be.

Figure 5:
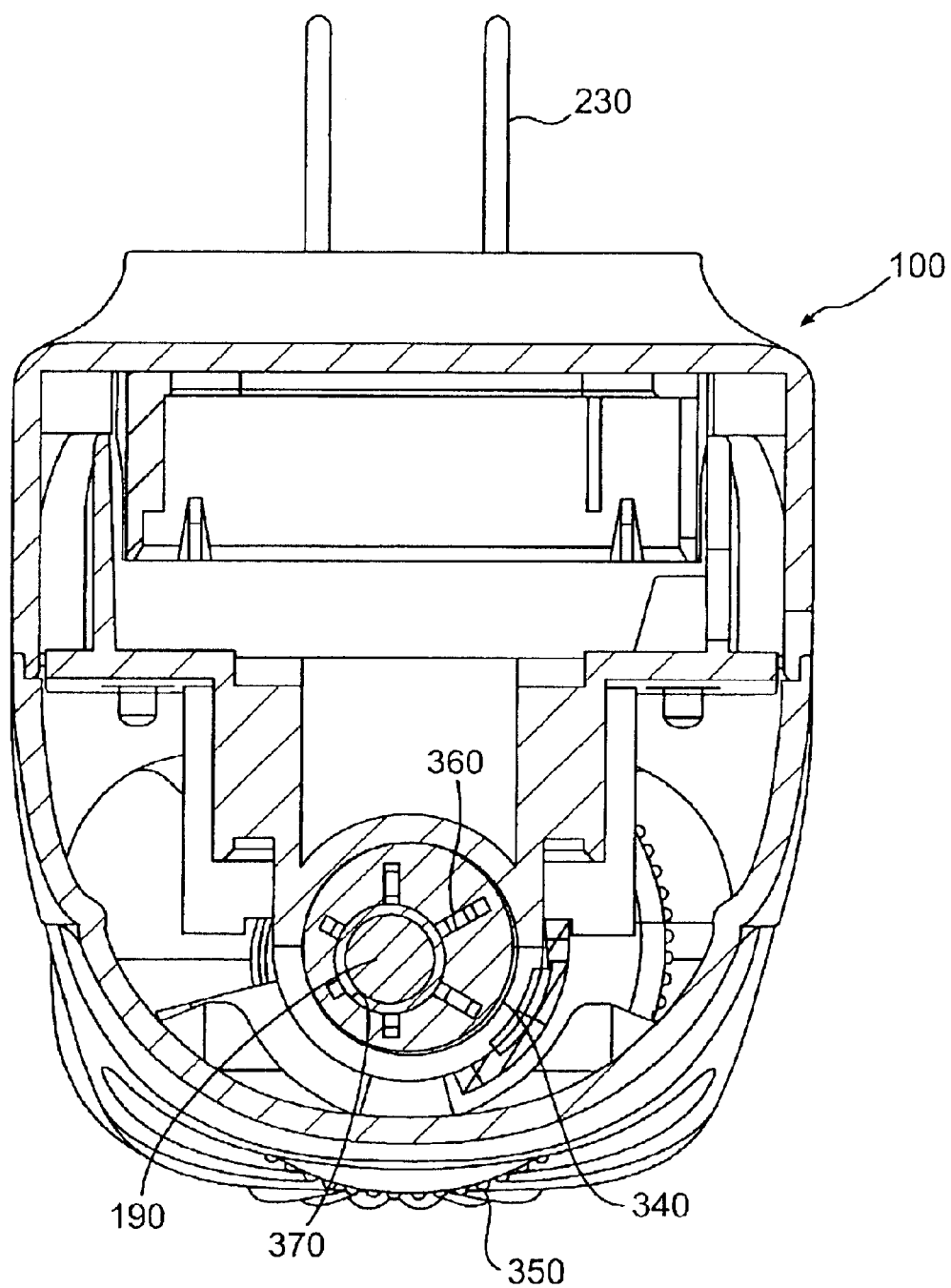
FIG. 5 is a cross-sectional view taken along section line A—A in FIG. 4.
Figure 6:
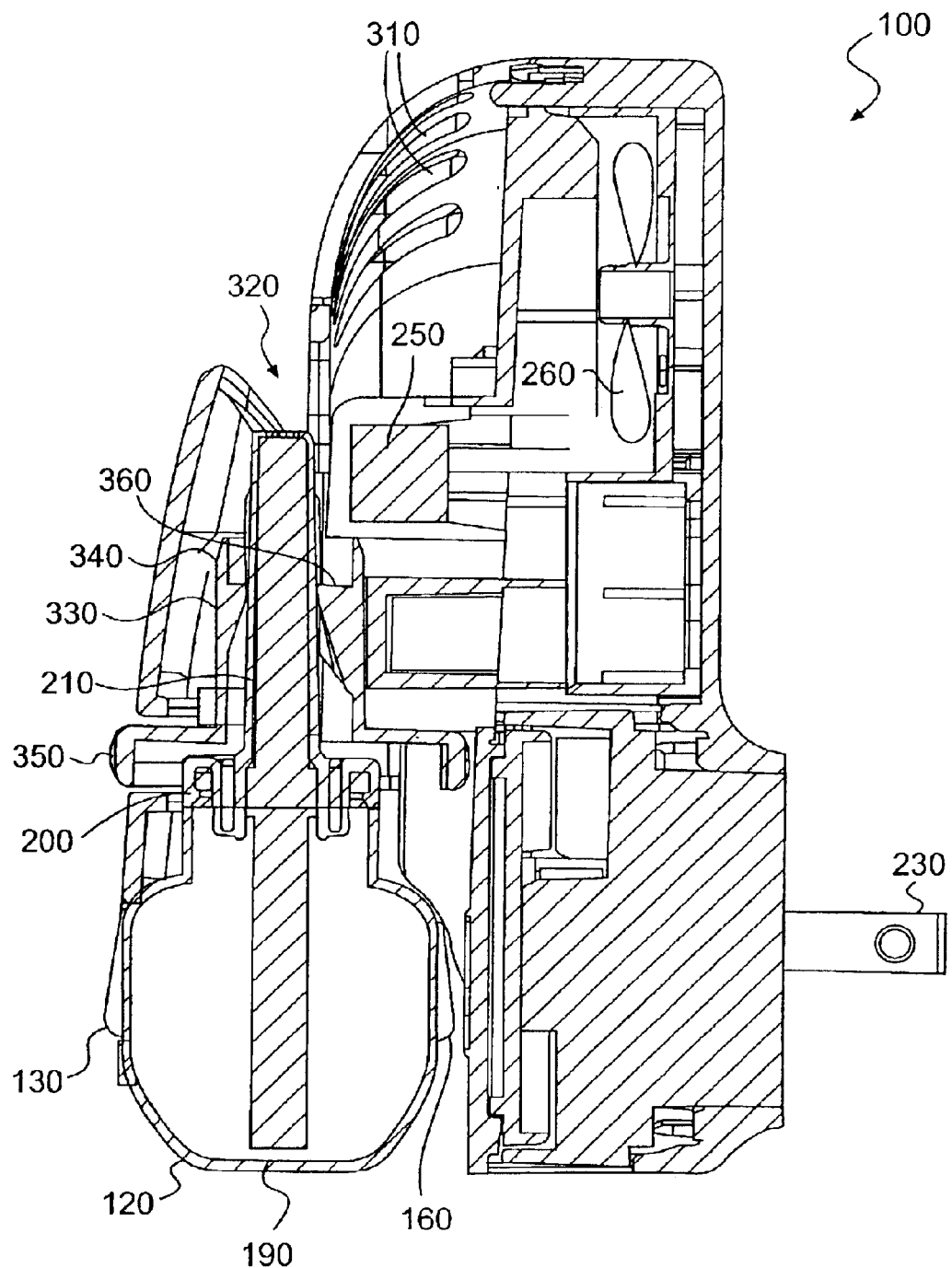
FIG. 6 is a cross-sectional view taken along section line B—B in FIG. 4.

Preferably, as shown in FIG. 5, a plurality of tapered lugs 360 is provided on the inner surface of the cylindrical portion 340. The lugs 360 are widest at their uppermost point, where they come in contact with the wick 190, and narrowest near the bottom of the cylindrical portion 340. At their uppermost point, the lugs 360 define a circular opening 370 that is just large enough for the wick 190 to fit through. The center of this opening 370 is offset relative to the axis of rotation of the cylindrical portion 340.

Figure 7:
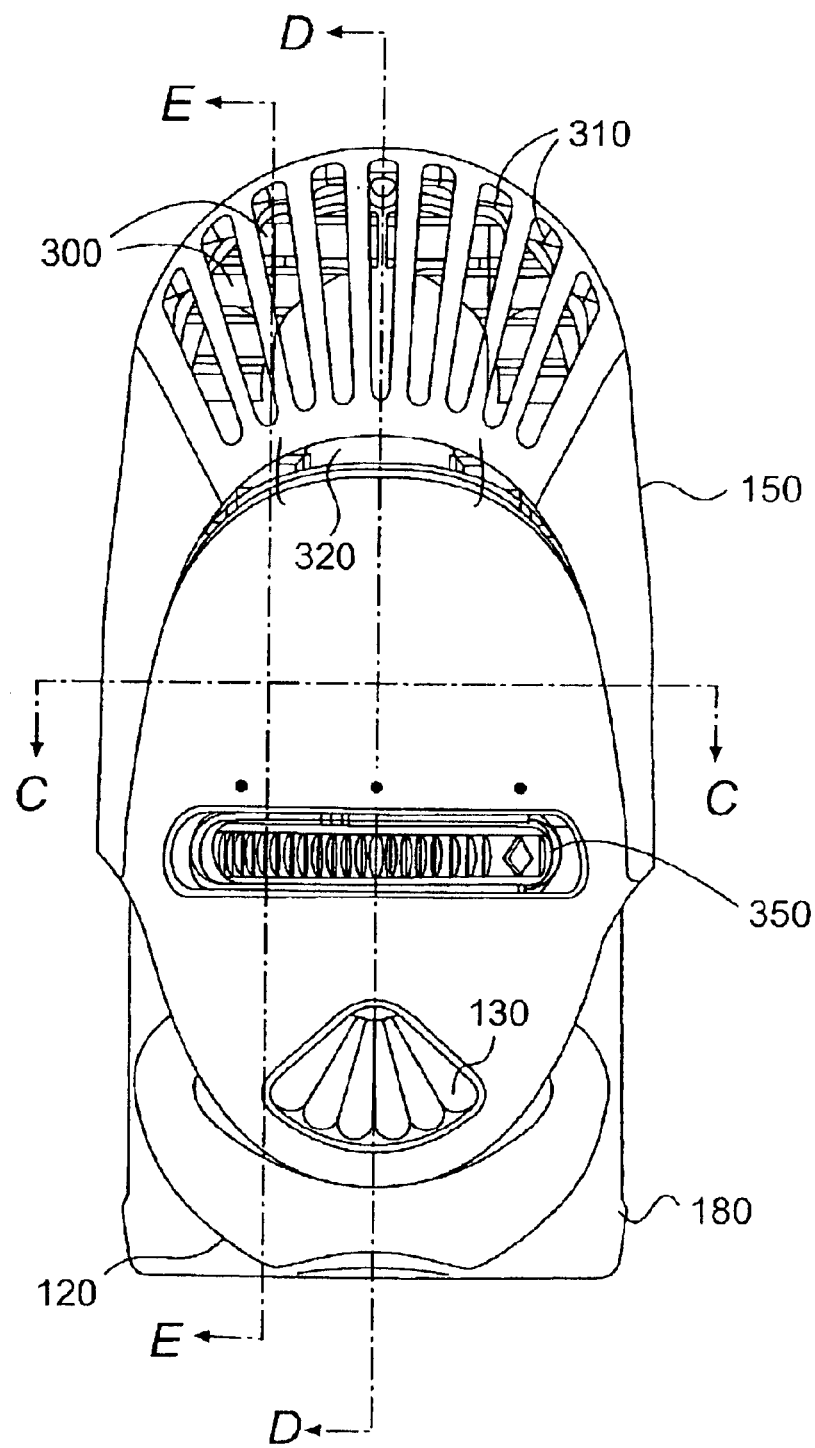
FIG. 7 is a front elevation view of the evaporator shown in FIG. 1, with the intensity setting on high.
Figure 8:
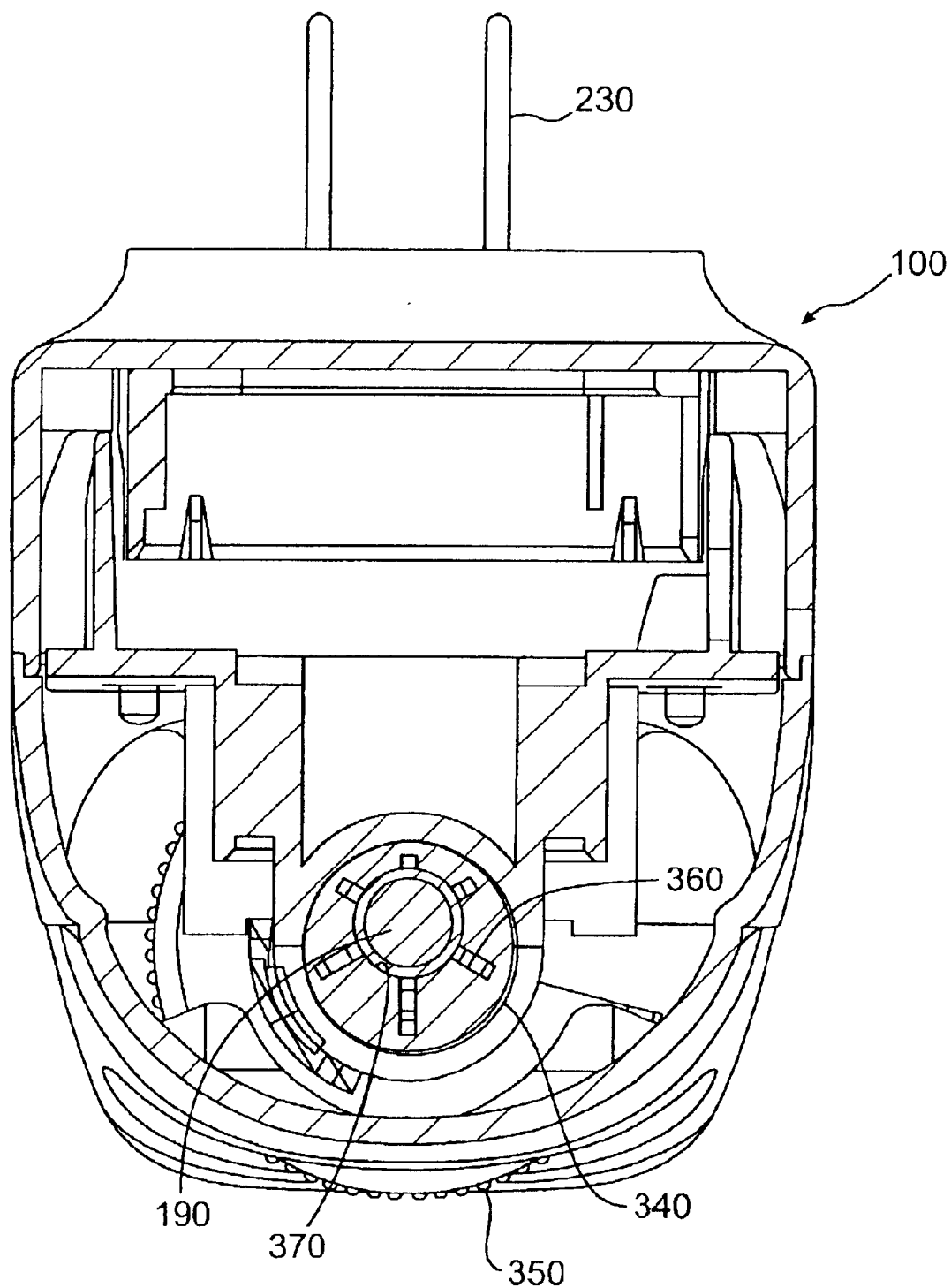
FIG. 8 is a cross-sectional view taken along section line C—C in FIG. 7.
Figure 9:
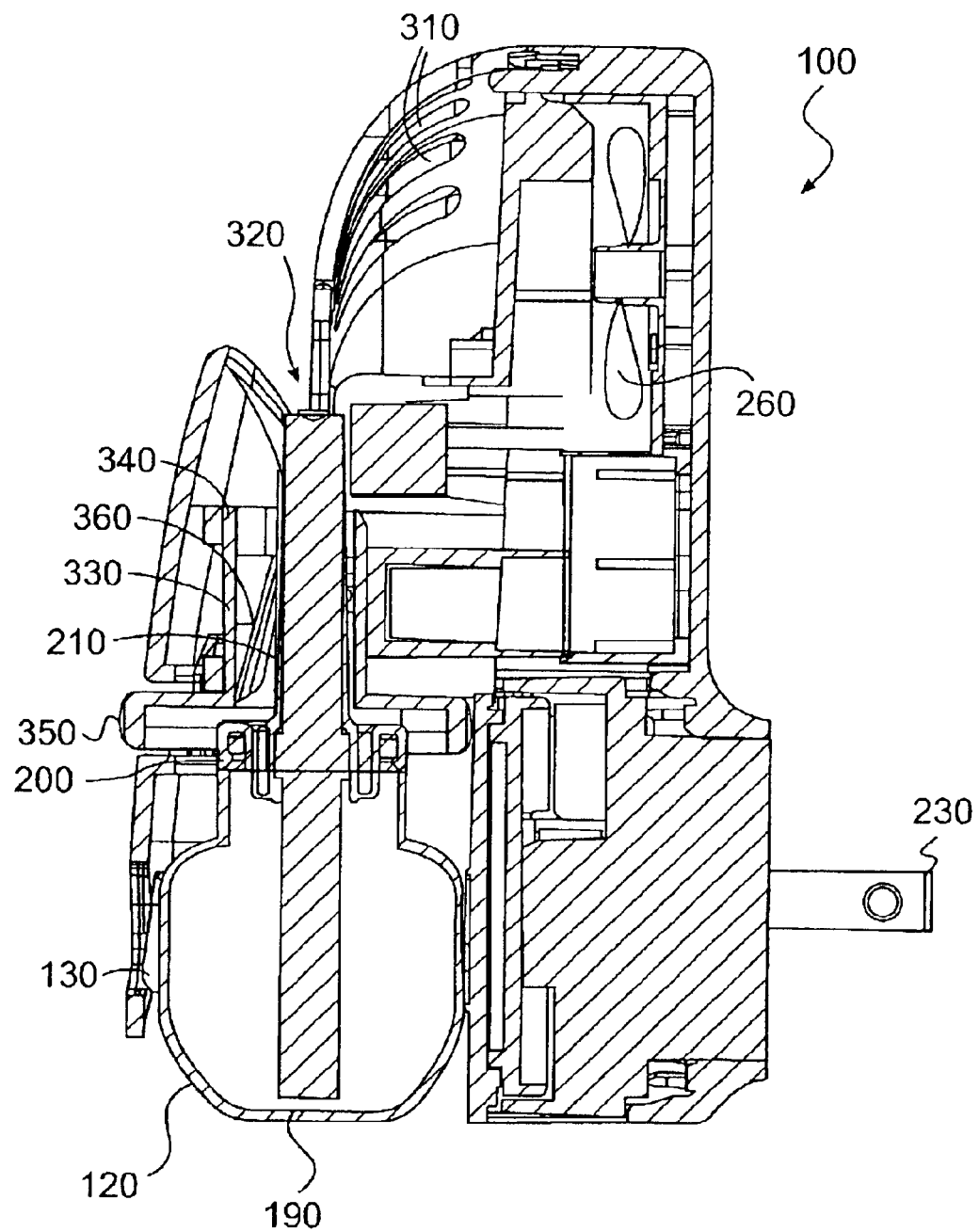
FIG. 9 is a cross-sectional view taken along section line D—D in FIG. 7.

Rotating the dial portion 350 of the adjustment mechanism 330 causes the wick 190 to move toward or away from the heating device 250 in a lateral direction, i.e., in a direction substantially perpendicular to the longitudinal axis of the wick 190. In the minimum intensity setting illustrated in FIGS. 4–6, the axis of the wick 190 is positioned about 6.3 mm from the heating device 250. In this position, the wick is heated to a temperature of about 71–78 C. Rotating the dial portion 350 approximately 75 degrees to the right brings the wick axis to a position that is about 4.4 mm from the heating device 250. At this maximum setting, which is illustrated in FIGS. 7–9, the wick is heated to a temperature of about 85–90 C, thereby resulting in a higher evaporation rate. The evaporator 100 also can be set to an intensity level anywhere in between the minimum and maximum settings. The lateral distance traveled by the wick 190 in moving from the minimum intensity setting to the maximum intensity setting is preferably between about 1 mm and about 3.5 mm. In the particular preferred embodiment described above, the lateral distance traveled by the wick 190 is about 2 mm.

Weight loss tests have demonstrated that the evaporation rate is almost 300 percent higher at the maximum setting than at the minimum setting.

A second preferred embodiment of the present invention is illustrated in FIGS. 12–17.

In this embodiment, the evaporator 1100 comprises an external housing 1110 including a top shell 1380 and a bottom shell 1390, which are snap-fit together. A rotatable plug assembly 1230 is located between the two shells 1380, 1390. The plug assembly 1230, which is of a type widely known in the industry, supplies electrical power to a heating device 1250 that is steadily housed within the top shell 1380.

The bottom shell 1390 is devoid of a bottom wall so as to allow insertion of a bottle 1120 therein. The bottle 1120, once it has been inserted into the shell 1390 and has been fastened thereto, forms an integral part of the evaporator 1100 and also serves as a support base when the evaporator 1100 is removed from a wall outlet and placed on a surface. In order to obtain stable fastening and firm locking of the bottle 1120 inside the shell 1390, a pair of opposing hook elements 1400 is employed. The hook elements 1400 engage the underside of a thin annular rib 1410 formed on the neck of the bottle 1120 when the bottle 1120 is inserted into the shell 1390.

The hook elements 1400 terminate, on the opposite side to the hook-shaped end, in a pushbutton 1420, which protrudes from the housing 1110 along the line of separation between the two shells 1380, 1390. The hook elements 1400, which preferably are formed integrally with the shell 1390, are attached to the shell 1390 by thin bridge pieces 1430 near the center of the hook elements 1400. Making use of their flexibility, the hook elements 1400 thus are able to pivot about the bridge pieces 1430, between an engaged position, shown in FIG. 13, and a splayed position in which the hook elements 1400 release the rib 1410, thereby allowing the bottle 1120 to be extracted from the shell 1390. The bottle 1120 fits precisely within the bottom shell 1390, making it impossible to laterally displace the bottle 1120. Therefore, extraction of the bottle can only be accomplished by simultaneously pressing the two pushbuttons 1420 in the direction of the arrows P in FIG. 13. This safety feature prevents accidental extraction of the bottle 1120 by young children.

Figure 15:
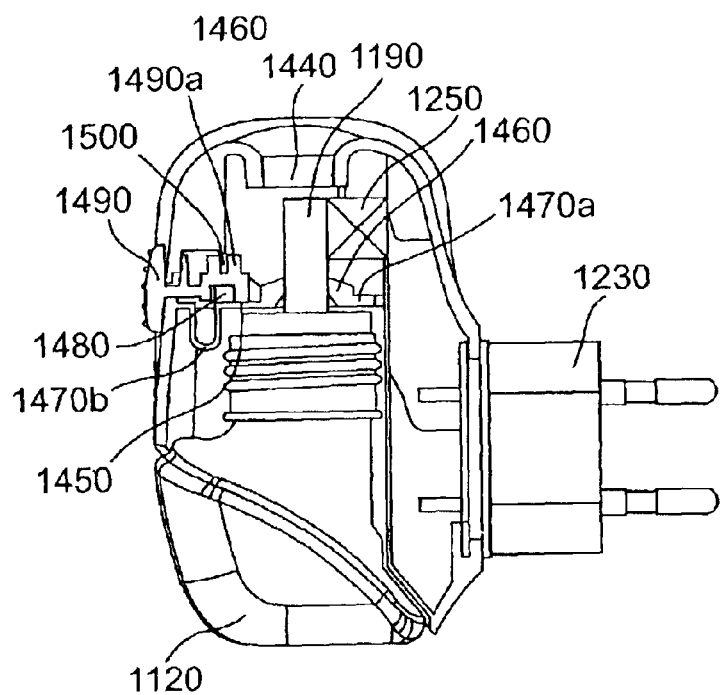
FIG. 15 is a cross-sectional view taken along section line F—F in FIG. 13.

As shown in FIG. 15, the top shell 1380 has in its top wall a central flue hole 1440 from which the vapors of the active substance emitted from the wick 1190 emerge. The hole 1440 preferably has a diameter that is larger than that of the wick 1190, so as to be able to embrace the various possible positions which the wick 1190 may assume, as will become clear from the description below.

In this embodiment of the present invention, the wick 1190 is housed and centered within the evaporator 1100 by an adjustment mechanism 1330 comprising an annular support 1450, which has projecting therefrom several fingers 1460 which come into contact with the lateral surface of the wick 1190, thereby positioning the wick 1190 with respect to the heating device 1250. The annular support 1450 preferably is formed integrally with the bottom shell 1380 and is joined thereto by means of plastic bridge pieces 1470a, 1470b. The bridge pieces 1470a, 1470b are sufficiently elastic to allow small displacements of the annular support 1450 and, together therewith, the wick 1190, toward or away from the heating device 1250 in a direction perpendicular to the axis of the wick 1190.

Figure 17:
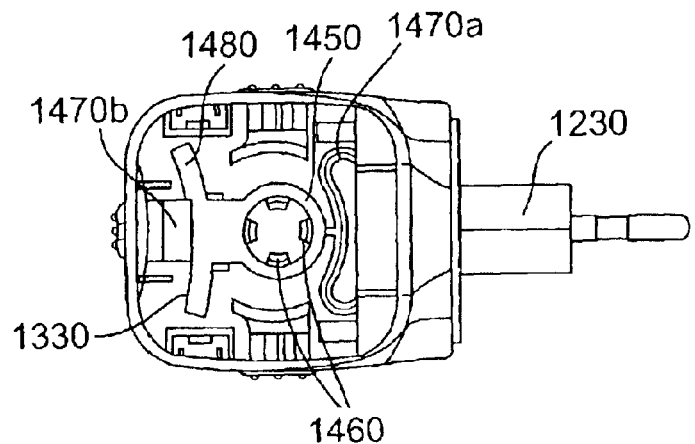
FIG. 17 is a bottom plan view of the evaporator shown in FIG. 12, again showing the evaporator adjustment mechanism.
Figure 16:
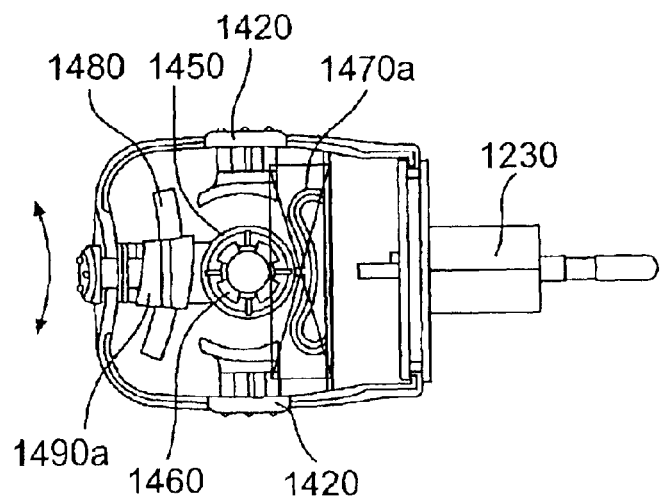
FIG. 16 is a top plan view of the evaporator shown in FIG. 12, with the top shell removed, in order to show the evaporator adjustment mechanism.

More particularly, the bridge pieces 1470a, 1470b have different shapes in order to ensure that the possibility of displacement of the annular support 1450 in the desired direction may be accompanied by excellent stability thereof as regards unwanted displacements in the other two possible directions. Specifically, the bridge piece 1470a has the shape of a loop in a horizontal plane, as shown in FIGS. 16 and 17, which prevents displacements of the support 1450 in a vertical direction. Meanwhile, the bridge piece 1470b has the shape of a loop in a vertical plane, as shown in FIG. 15, which prevents displacements of the support 1450 in the other direction perpendicular to the axis of the wick 1190, i.e., the direction parallel to the longitudinal axis of the heating device 1250. The desired displacements of the annular support 1450 may be effected by the user with the aid of a cam device. This device consists of a cam profile 1480, in the form of an arc with a varying radius, formed integrally with the annular support 1450, and a cam-following cursor 1490, which is formed as a single piece separate from the shells 1380, 1390 and has an outer operating pushbutton and an inner end 1490a intended to cooperate with the cam profile 1480. The inner end 1490a has a pair of opposing grooves, one of which is guided by a profiled arc 1500 having a constant radius, formed integrally with the top shell 1380, while the opposite groove determines the position of the cam profile 1480, causing the movement of the support 1450 and with it the wick 1190 away from or toward the heating device 1250.

The evaporator having the above described structure can be produced by means of a simple molding process involving three elements: namely, the two shells 1380, 1390, complete with all of the necessary detailed parts for obtaining the desired adjustment of the flow, as well as the cursor 1490 for actuating the cam device. The manufacturing costs associated with this evaporator, therefore, are much lower than the manufacturing costs of known adjustable-flow evaporators and basically substantially the same as that of an evaporator without a flow adjustment feature.

By moving the sliding pushbutton of the cursor 1490 it is therefore possible to adjust the position of the annular support 1450, and thus of the wick 1190, in any desired position between the position closest to the heating device 1250, which is the maximum outflow position, and a minimum outflow position, which may obviously be varied during design, depending on the type of evaporator, by simply modifying the curvature of the variable-radius cam profile 1480.

It should also be noted that operation of the cursor 1490 is of the non-reversible type, and, therefore, the associated pushbutton may be steadily arranged in any intermediate position—from which it does not move unless actuated again by the operator—thus allowing the user to perform continuous, stable, and repeatable adjustment of the flow of active substance emitted, between the minimum and maximum levels.

Finally, the special system for fastening and locking the bottle 1120 within the evaporator 1100 is not only extremely simple and inexpensive, but also very safe vis-à-vis young children. Activation of the locking system is in fact performed by simply pressing the bottle 1120 into the evaporator housing 1110, since the annular rib 1410 splays the hook elements 1400, acting on their inclined external surface. Once fastening has been performed, release of the bottle is possible only by simultaneously pressing the two pushbuttons 1420 in opposite directions, which is a difficult operation for a child to perform.

The embodiments discussed above are representative of preferred embodiments of the present invention and are provided for illustrative purposes only. They are not intended to limit the scope of the invention. Although specific structures, dimensions, components, etc., have been shown and described, such are not limiting. Modifications and variations are contemplated within the scope of the present invention, which is intended to be limited only by the scope of the accompanying claims.

INDUSTRIAL APPLICABILITY

The present invention provides an electrical evaporator for use with liquid formulations containing a chemical active such as an insecticide, fragrance, or the like. The evaporator includes an improved adjustment mechanism for varying the evaporation rate of the liquid formulation. Thus, the concentration of the chemical active dispersed into the surrounding environment can be precisely controlled, depending on a user's preferences.

We claim:

1. An evaporator, for use with a bottle containing a substance to be evaporated and a wick that has its lower portion disposed within the bottle and its upper portion protruding from the bottle, the evaporator comprising:
   a housing;
   a heating device disposed within the housing at a position proximate to the upper portion of the wick; and
   an adjustment mechanism within the housing for displacing at least the upper portion of the wick toward or away from the heating device in a direction substantially perpendicular to the longitudinal axis of the wick.

2. The evaporator of claim 1, wherein the adjustment mechanism includes an opening through which the wick extends.

3. The evaporator of claim 1, wherein the bottle is detachably engaged within the housing.

4. The evaporator of claim 1, wherein the substance to be evaporated is one of an insecticide, a fragrance, or an odor eliminator.

5. The evaporator of claim 1, wherein the adjustment mechanism includes a hollow cylindrical portion that surrounds at least part of the upper portion of the wick and a dial portion for rotating the hollow cylindrical portion about an axis of rotation.

6. The evaporator of claim 5, wherein the dial portion is formed integrally with the hollow cylindrical portion.

7. The evaporator of claim 5, wherein the hollow cylindrical portion is rotatable through a range of rotation of about 75 degrees.

8. The evaporator of claim 5, wherein the hollow cylindrical portion defines an opening through which the wick extends, and the center of the opening is offset relative to the axis of rotation of the hollow cylindrical portion.

9. The evaporator of claim 5, wherein the adjustment mechanism further includes a plurality of tapered lugs disposed on an inner surface of the hollow cylindrical portion in contact with the upper portion of the wick.

10. The evaporator of claim 3, wherein the distance between the upper portion of the wick and the heating device can be varied by about 1 mm to about 3.5 mm.

11. The evaporator of claim 10, wherein the distance between the upper portion of the wick and the heating device can be varied by about 2 mm.

12. The evaporator of claim 5, further comprising a sheath encasing at least part of the upper portion of the wick.

13. The evaporator of claim 3, further comprising a fan disposed within the housing.

14. The evaporator of claim 1, further comprising an electrical plug for supplying power to the heating device and for supporting the evaporator in a wall outlet.

15. The evaporator of claim 14, wherein the electrical plug is rotatable in order to support the evaporator in an upright position in both horizontal and vertical wall outlets.

16. An evaporator, comprising:
  a housing;
  a bottle containing a substance to be evaporated;
  a wick, having a lower portion disposed within the bottle and an upper portion protruding from the bottle, for drawing the substance to be evaporated toward the upper portion of the wick;
  means for heating the upper portion of the wick to evaporate the substance;
  means for positioning the upper portion of the wick relative to the heating means; and
  means for displacing at least the upper portion of the wick toward or away from the heating means in a direction substantially perpendicular to the longitudinal axis of the wick.

17. The evaporator of claim 16, wherein the bottle is detachably engaged within the housing.

18. The evaporator of claim 16, wherein the substance to be evaporated is one of an insecticide, a fragrance, or an odor eliminator.

19. The evaporator of claim 16, wherein the displacing means includes:
  a hollow cylindrical portion that surrounds at least part of the upper portion of the wick; and
  a dial portion for rotating the hollow cylindrical portion about an axis of rotation.

20. The evaporator of claim 19, wherein the dial portion is formed integrally with the hollow cylindrical portion.

21. The evaporator of claim 19, wherein the hollow cylindrical portion is rotatable through a range of rotation of about 75 degrees.

22. The evaporator of claim 19, wherein the hollow cylindrical portion defines an opening through which the wick extends, and the center of the opening is offset relative to the axis of rotation of the hollow cylindrical portion.

23. The evaporator of claim 19, wherein the displacing means further includes a plurality of tapered lugs disposed on an inner surface of the hollow cylindrical portion in contact with the upper portion of the wick.

24. The evaporator of claim 19, wherein the distance between the upper portion of the wick and the heating means can be varied by about 1 mm to about 3.5 mm.

25. The evaporator of claim 19, wherein the distance between the upper portion of the wick and the heating means can be varied by about 2 mm.

26. The evaporator of claim 19, further comprising a fan disposed within the housing.

27. The evaporator of claim 16, further comprising a sheath encasing at least part of the upper portion of the wick.

28. The evaporator of claim 16, further comprising an electrical plug for supplying power to the heating means and for supporting the evaporator in a wall outlet.

29. The evaporator of claim 16, wherein the electrical plug is rotatable in order to support the evaporator in an upright position in both horizontal and vertical wall outlets.

30. A plug-in evaporator for vaporizing a liquid formulation, comprising:
  a bottle containing a liquid formulation;
  a wick, having a lower portion disposed within the bottle and an upper portion protruding from the bottle, for drawing the liquid formulation from the bottle toward the upper portion of the wick; and
  a housing in which the bottle is retained, the housing including (i) an electrical heating device positioned proximate to the upper portion of the wick, (ii) an electrical plug for supplying power to the heating device and for supporting the evaporator in a wall outlet, and (iii) an adjustment mechanism for displacing the upper portion of the wick toward or away from the heating device in a direction substantially perpendicular to the longitudinal axis of the wick.

31. The evaporator of claim 30, wherein the adjustment mechanism includes an opening through which the wick extends.

32. The evaporator of claim 30, wherein the bottle is detachably retained within the housing.

33. The evaporator of claim 30, wherein the liquid formulation is one of an insecticide, a fragrance, or an odor eliminator.

34. The evaporator of claim 30, wherein the adjustment mechanism includes a hollow cylindrical portion that surrounds at least part of the upper portion of the wick and a dial portion for rotating the hollow cylindrical portion about an axis of rotation.

35. The evaporator of claim 34, wherein the dial portion is formed integrally with the hollow cylindrical portion.

36. The evaporator of claim 34, wherein the hollow cylindrical portion is rotatable through range of rotation of about 75 degrees.

37. The evaporator of claim 34, wherein the hollow cylindrical portion defines an opening through which the wick extends, and the center of the opening is offset relative to the axis of rotation of the hollow cylindrical portion.

38. The evaporator of claim 34, wherein the distance between the upper portion of the wick and the heating device can be varied by about 1 mm to about 3.5 mm.

39. The evaporator of claim 38, wherein the distance between the upper portion of the wick and the heating device can be varied by about 2 mm.

40. The evaporator of claim 34, further comprising a sheath encasing at least part of the upper portion of the wick.

41. The evaporator of claim 34, wherein the housing further includes a fan.

42. The evaporator of claim 34, wherein the adjustment mechanism further includes a plurality of tapered lugs disposed on an inner surface of the hollow cylindrical portion in contact with the upper portion of the wick.

43. The evaporator of claim 30, wherein the electrical plug is rotatable in order to support the evaporator in an upright position in both horizontal and vertical wall outlets.

44. A plug-in evaporator for dispersing a chemical active into a surrounding environment, comprising:
- a bottle containing a liquid formulation;
- a wick, having a lower portion disposed within the bottle and an upper portion protruding from the bottle, for drawing the liquid formulation from the bottle toward the upper portion of the wick;
- a housing in which the bottle is detachably retained;
- an electrical heating device disposed within the housing at a position proximate to the upper portion of the wick;
- an electrical plug extending from the housing for supplying power to the heating device and for supporting the evaporator in a wall outlet; and
- an adjustment mechanism within the housing for displacing the upper portion of the wick toward or away from the heating device in a direction substantially perpendicular to the longitudinal axis of the wick, the adjustment mechanism including (i) a hollow cylindrical portion that engages the upper portion of the wick, and (ii) a dial portion for rotating the hollow cylindrical portion about an axis of rotation,
- wherein the hollow cylindrical portion defines an opening through which the wick extends, and the center of the opening is offset relative to the axis of rotation of the hollow cylindrical portion.

45. The evaporator of claim 44, wherein the liquid formulation is one of an insecticide, a fragrance, or an odor eliminator.

46. The evaporator of claim 44, wherein the dial portion is formed integrally with the hollow cylindrical portion.

47. The evaporator of claim 44, wherein the hollow cylindrical portion is rotatable through a range of rotation of about 75 degrees.

48. The evaporator of claim 44, wherein the adjustment mechanism further includes a plurality of tapered lugs disposed on an inner surface of the hollow cylindrical portion in contact with the upper portion of the wick.

49. The evaporator of claim 44, wherein the distance between the upper portion of the wick and the heating device can be varied by about 1 mm to about 3.5 mm.

50. The evaporator of claim 49, wherein the distance between the upper portion of the wick and the heating device can be varied by about 2 mm.

51. The evaporator of claim 44, further comprising a sheath encasing at least part of the upper portion of the wick, wherein hollow cylindrical portion of the adjustment mechanism engages a part of the wick encased by the sheath.

52. The evaporator of claim 44, further comprising a fan disposed within the housing.

53. The evaporator of claim 44, wherein the electrical plug is rotatable in order to support the evaporator in an upright position in both horizontal and vertical wall outlets.

* * * * *